(12) United States Patent
Besendorfer

(10) Patent No.: US 8,062,676 B2
(45) Date of Patent: Nov. 22, 2011

(54) PESTICIDE COMPOSITION

(76) Inventor: Thomas Besendorfer, Munich (DE)

( * ) Notice: Subject to any disclaimer, the term of this patent is extended or adjusted under 35 U.S.C. 154(b) by 694 days.

(21) Appl. No.: 12/023,420

(22) Filed: Jan. 31, 2008

(65) Prior Publication Data

US 2008/0181968 A1 Jul. 31, 2008

Related U.S. Application Data

(63) Continuation-in-part of application No. PCT/EP2006/006331, filed on Jun. 29, 2006.

(60) Provisional application No. 60/954,938, filed on Aug. 9, 2007.

(30) Foreign Application Priority Data

Aug. 2, 2005 (WO) ................ PCT/EP2005/008360

(51) Int. Cl.
*A01N 39/00* (2006.01)
*A61K 33/40* (2006.01)
(52) U.S. Cl. .................. 424/616; 424/405; 514/613
(58) Field of Classification Search .................. None
See application file for complete search history.

(56) References Cited

U.S. PATENT DOCUMENTS

| 4,839,098 | A  | * | 6/1989  | Wisotzki et al. | ............... | 510/235 |
| 6,455,075 | B1 | * | 9/2002  | Larose          | ................ | 424/616 |
| 6,599,941 | B1 | * | 7/2003  | James et al.    | ................ | 514/563 |
| 2003/0060379 | A1 | * | 3/2003  | Souter et al. | ................ | 510/131 |
| 2003/0224939 | A1 | * | 12/2003 | Miles         | ................ | 504/206 |
| 2005/0008714 | A1 | * | 1/2005  | Enan          | ................ | 424/745 |
| 2005/0106190 | A1 | * | 5/2005  | Kawa et al.   | ................ | 424/401 |

FOREIGN PATENT DOCUMENTS

| WO | WO 9944425 A1 | * | 9/1999 |
| WO | WO 0209670 A1 | * | 2/2002 |

OTHER PUBLICATIONS

Wang, Shuo, et al., Development of a Class-Specific ELISA for the Benzoylphenylurea Insecticides, 1998, J. Agric. Food Chem. 46, 3330-3338.*

Mikolajczyk, Piotr, et al., Chitin SYnthesis in *Spodoptera frugiperda* Wing Imaginal Discs: I. Chlorfluazuron, Diflubenzuron, and Teflubenzuron Inhibit Incorporation but not Uptake of [14C]N-acetyl-D-glucosamine, 1994, Arch. Insect Biochem. Physiol. 25, 245-258.*

* cited by examiner

*Primary Examiner* — Johann Richter
*Assistant Examiner* — Thor Nielsen
(74) *Attorney, Agent, or Firm* — Downs Rachlin Martin PLLC

(57) ABSTRACT

Stable non-toxic pesticide composition having fungicidal and insecticidal properties including a pesticide that is nontoxic to mammals; one or more disinfectants; a vegetable oil; and one or more stabilizing agents. In one example, one or more stabilizing agents are selected and are present in an amount in combination with the selection and amount of a pesticide, one or more disinfectants, and a vegetable oil to provide the composition with stability upon application to a substrate effective to allow lethality against one or more target pests.

14 Claims, No Drawings

PESTICIDE COMPOSITION

RELATED APPLICATION DATA

This application is a continuation in part of PCT Application Serial No. PCT/EP2006/006331, filed Jun. 29, 2006, entitled "Composition with a Bactericidal, Fungicidal, Viricidal and Insecticidal Action and Composition Acting as a Repellant," which claims priority to PCT Application Serial No. PCT/EP2005/008360, Aug. 2, 2005, entitled "Composition Having Bactericidal, Fungicidal, Virucidal and Insecticidal Action," both of which applications are incorporated by reference herein in their entirety. This application also claims the benefit of U.S. Provisional Patent Application Ser. No. 60/954,938, filed Aug. 9, 2007, which application is incorporated by reference in its entirety.

FIELD OF THE INVENTION

The present invention generally relates to the field of a pesticide compositions. Composition. In particular, the present invention is directed to a pesticide composition with fungicidal, disinfectant, and repellant properties.

BACKGROUND

Conventional methods of eliminating pests (e.g., fungi, mosquitoes, flies, wasps, woodlice, bugs, beetles, grasshoppers, locusts) are toxic, carcinogenic, teratonogenic, expensive, and/or inefficient. Although many toxic pesticides (e.g., DDT, Lindan, Chlordan, etc.) are relatively inexpensive, they leave behind contamination in ground soil, water, plants and other substrates to which they may be applied in an attempt to come into contact with the target pests. This contamination works its way into humans and other mammals directly and up through the food chain. In some cases pesticide contamination can be measured in an area of application many years later.

Attempts have been made to utilize biological pesticides to mitigate the contamination that is known with toxic pesticides. However, biological pesticides suffer from poor stability over time in storage and after application. Thus, their efficacy has been limited to short-term, immediate uses.

The term "disinfectant" stands for substances or mixtures of substances for combating pathogenic microorganisms, or microorganisms that cause putrefaction, e.g. bacteria, viruses, fungus including spores. Disinfectants can minimize the risk of an infection of humans or animals, or minimize the onset of putrefaction. Since some bacteria, molds, yeasts and viruses can lead to severe diseases, disinfection cannot be dismissed from the everyday life in the medical sector and private households. The importance of disinfection for the well being of humans is often underestimated. In previous centuries more people died as a result of the large epidemics (the plague, cholera, pox or the flu) than were killed during the wars. As late as the beginning of the 20th century, severe bacterial infections were often a deadly disease even in the industrialized nations. In the countries of the so-called third world even today infectious diseases, mostly stemming from inadequate hygienic situations, claim countless deaths. Therefore a high demand for effective and inexpensive disinfectants exists, especially in the medical sector. This demand also exists in the agrarian sector particularly for fungicidal substances.

In order to obtain a highly disinfectant effect, in the past, above all, highly persistent chemical composites were used as disinfectants in order to have an effective and long-lasting protection against microorganisms. But this persistence leads to huge problems with respect to environmental aspects. The highly persistent disinfectants accumulate in the groundwater and/or the food chain, and thereby lead to ecological and health problems. For example, ecological problems can arise when disinfectants in high concentration reach biological wastewater treatment plants. In case of high concentrations of this disinfectant the microorganisms, which are necessary there, are affected in their growth, which can lead to a partial or complete failure of the wastewater treatment plant. Furthermore, persistent composites can accumulate in the sewage sludge.

A further disadvantage of conventional disinfectants is the development of resistances. Resistant causative organisms survive the treatment with the disinfectant, and can pass on their resistance to non-resistant microorganisms via the transmittal of extra chromosomal genetic material. Disinfection of microorganisms, which have developed a resistance this way, can lead to severe diseases. While this problem can currently be observed mainly in the sectors of hospitals (hospitalism) and farm animals, one can fear that such problems in the future can also occur in the sector of private households, given the fact that disinfectants are used more and more in household cleaning agents.

In order to overcome the health and ecological disadvantages of such persistent disinfectants, the use of less dangerous substances has been considered in the past, especially the use of natural substances with potential for disinfectant properties. Here it has turned out to be a disadvantage that the disinfectant effect is weaker and/or less long lasting, so that the advantage of better environmental compatibility is gained in exchange for disadvantages in regards to effectiveness and protection from microorganisms. Due to this drawback, less importance has been awarded to such ecologically compatible disinfectants and the use of environmentally hazardous compounds prevail.

SUMMARY OF THE DISCLOSURE

In one embodiment, a stable non-toxic pesticide composition having fungicidal and insecticidal properties is provided. The composition includes a pesticide that is nontoxic to mammals; one or more disinfectants; a vegetable oil; and one or more stabilizing agents; wherein the one or more stabilizing agents are selected and are present in an amount in combination with the selection and amount of the pesticide, the one or more disinfectants, and the vegetable oil to provide the composition with a stability upon application to a substrate effective to allow lethality against one or more target pests and wherein the composition is fungicidally and insecticidally effective upon application to a substrate and has a chitin skeleton destructive capability.

In another embodiment, a stable non-toxic pesticide composition having fungicidal and insecticidal properties is provided. The composition includes a pesticide that is nontoxic to mammals; a chitin skeleton destructive compound; a vegetable oil; and one or more stabilizing agents; wherein the one or more stabilizing agents are selected and are present in an amount in combination with the selection and amount of the pesticide, the chitin skeleton destructive compound, and the vegetable oil to provide the composition with a stability upon application to a substrate effective to allow lethality against one or more target pests, and wherein the composition achieves at least about 100% effectiveness in lethality against one or more target pests at about 1 hour after application In yet another embodiment, a stable non-toxic pesticide composition having fungicidal and insecticidal properties is provided. The composition includes 10-30 wt. % geraniol; 5-25 wt. % PEG-20 glyceryl-oleoricinoleate; 20-40 wt. % of a reaction product of coconut fatty acids with a diethanolamide; 10-30 wt. % isooctyl-sulfosuccinate; and 1-20 wt. % soybean oil, wherein the composition achieves at least about 100% effectiveness in lethality against one or more target pests at about 1 hour after application.

DETAILED DESCRIPTION

In one embodiment, a pesticide composition includes a pesticide that is non-toxic to mammals, a chitin skeleton destructive compound, a vegetable oil, and one or more stabilizing agents. The pesticide composition is composed such that it has sufficient stability in storage and after application to a substrate for treating one or more pests. The pesticide composition itself has little to no toxicity to mammals.

A pesticide is a substance that is used to control and/or eliminate pests. Example pests include, but are not limited to, an insect (e.g., a mosquito, a fly, a wasp, an ant, a woodlice, a locust, a grasshopper, etc.), a fungus, other bugs (e.g., a spider, a centipede), other pests, and any combinations thereof. One or more of a variety of non-toxic pesticides may be utilized in a pesticide composition according to the present disclosure. Examples of non-toxic pesticides include, but are not limited to, geraniol, castor oil, cinnamon oil, citric acid, citronella oil, clove oil, corn oil, cotton seed oil, eugenol, garlic oil, geranium oil, lauryl sulfate, lemongrass oil, linseed oil, maleic acid, mint oil, peppermint oil, 2-phenethyl proprionate, sodium sorbate, rosemary oil, sesame oil, sodium lauryl sulfate, soybean oil, thyme oil, white pepper, octyl acid, decane acid, formic acid, propane-2-ol, rapeseed oil, lavandine oil, and any combinations thereof. In one example, a non-toxic pesticide includes geraniol.

A pesticide may be present in a composition according to the present disclosure in an amount sufficient to provide a pesticidal activity to the composition while allowing the composition to maintain an adequate level of stability in storage and upon application. In one example, a pesticide is present in a composition in an amount from about 10 weight (wt.) percent (%) to about 80 wt. %. In another example, a pesticide is present in a composition in an amount from about 0.5 wt. % to about 5 wt. %. In yet another example, a pesticide is present in a composition in an amount from 10 wt. % to 30 wt. %. In still another example, a pesticide is present in a composition in an amount of about 21 wt. %.

In an alternative embodiment, a composition may include sodium chloride in addition to one or more pesticides. It has been shown that the addition of sodium chloride to a composition can boost the pesticidal (e.g., insecticidal) effect of the composition.

A pesticide composition according to the present disclosure may have a chitin skeleton destructive capability. A chitin skeleton destructive capability allows a pesticide composition to destabilize the chitin structures that make up a skeleton (cuticula) of a pest. Without wanting to commit to a theory, the applicant postulates that one or more chitin skeleton destructive compounds included in a pesticide composition may contribute to a chitin skeleton destructive capability. A chitin skeleton destructive compound is a substance that is capable of destabilizing the chitin structures that make up a skeleton (cuticula) of a pest. In one example, a chitin skeleton destructive compound attacks and/or softens a chitin skeleton by cracking poly-n-acetylglucosamine structures within the skeleton. It is believed that examples of a chitin skeleton destructive compound include, but are not limited to, a reaction product of a coconut fatty acid with a diethanolamine. In one example, a composition according to the present disclosure includes a chitin skeleton destructive compound that includes a reaction product of a coconut fatty acid with a diethanolamine. In another example, a composition according to the present disclosure includes a chitin skeleton destructive compound that includes a reaction product of a coconut fatty acid with a diethanolamine having the CAS-number 68440-04-0.

A chitin skeleton destructive compound may be present in a composition according to the present disclosure in an amount sufficient to provide the composition with an ability to destabilize a chitin structure of a skeleton of a pest. In one example, a chitin skeleton destructive compound is present in a composition in an amount from about 20 wt. % to about 80 wt. %. In another example, a chitin skeleton destructive compound is present in a composition in an amount from about 0.75 wt. % to about 8 wt. %. In yet another example, a chitin skeleton destructive compound is present in a composition in an amount from about 20 wt. % to about 40 wt. %. In still another example, a chitin skeleton destructive compound is present in a composition in an amount of about 31 wt. %.

Examples of a vegetable oil that may be used in a composition as disclosed herein include, but are not limited to, soybean oil, safflower oil, olive oil, linseed oil, cottonseed oil, corn oil, coconut oil, cod liver oil, castor oil, hydrogenated castor oil, peanut oil, sperm oil, cocoa, palm-oil, wheat germ oil, sweet almond oil, sesame oil, hydrogenated soybean oil, soy lecithin, white mineral oil, hydrogenated cottonseed oil, hydrogenated palm-oils, rice bran oil, wheat oils, wintergreen oil, hydrogenated rapeseed oil, canola oil, hydrogenated castor oil, and any combinations thereof.

In one example, a vegetable oil is present in an amount effective to provide a physiochemical ability to the composition to interfere with one or more neurotransmitters of a pest that comes into contact with the composition. In another example, a vegetable oil is present in an amount of about 1 wt. % to about 80 wt. %. In yet another example, a vegetable oil is present in an amount of about 10 wt. % to about 20 wt. %. In still another example, a vegetable oil is present in an amount of about 11 wt. %.

A stabilizing agent may work in combination with other components of a composition according to the present disclosure to provide stability to the composition and to its components (e.g., stabilizing the storage life of a vegetable oil). Examples of a stabilizing agent include, but are not limited to, an emulsifier, a dissolving substance, a moist keeping agent, L-ascorbic acid, hexadecane acid, stearic acid, urea, calcium acetate, sodium citrate, citric acid, fumaric acid, olein acid, potassic acetate, sodium acetate, lauric acid, a disodium salt of citric acid, sodium bicarbonate, potassium bicarbonate, calcium carbonate, myristic acid, magnesium carbonate, magnesium stearate, zinc stearate, calcium citrate, a monopotassic salt of citric acid, a dipotassic salt of citric acid, a tri-potassic salt of citric acid, potassium citrate, ammonium stearate, magnesium oxide, zinc oxide, calcium stearate, maleic acid, potassium chloride, magnesium sulfate, potassium bisulfate, sodium chloride, calcium citrate, a disodium salt of sulfuric acid, sodium sulfate, potassium sulfate, a cyclodextrine, glyceril monostearate, sorbitol, decamine oxide, PEG-4 monophenyl ether, PEG-20 glyceryl-oleoricinoleate, sorbic acid, sorbitane monolaurate, sorbitane monooleate, polyglycerol-4 oleate, a cocamine, tridecyl alcohol, lauryl alcohol, trideceth-9, lactic acid, and any combinations thereof. Examples of an emulsifier/dissolving substance include, but are not limited to, glycerin, soybean oil, safflower oil, olive oil, linseed oil, cottonseed oil, corn oil, coconut oil, cod liver oil, castor oil, hydrogenated castor oil, peanut oil, sperm oil, cocoa, lecithin, malt extract, palm-oil, lanolin, wheat germ oil, sweet almond oil, sesame oil, hydrogenated soybean oil, soy lecithin, white mineral oil, molasses, hydrogenated cottonseed oil, hydrogenated palm-oils, rice bran oil, wheat oils, wintergreen oil, hydrogenated rapeseed oil, canola oil, cetyldimethiconcopolyol, PEG-20 glyceryl-oleoricinoleate, pentylene glycol, PEG-40, PEG-60, hydrogenated castor oil, propylene glycol, and any combinations thereof. Examples of moist keeping agent include, but are not limited to, dimethiconpropyl PG-betaine, quaternium-80, dimethiconcopolyol, sterayldimethicon, cetyldimethicon, capraamidoalkylbetaine, sodium isooctylsulfate, sodium diisooctylsulfosuccinate, sodium dioctylsulfosuccinate, a sodium salts of sulfosuccinate, isooctyl-sulfosuccinate, and any combinations thereof. In one example, a composition according to the present disclosure includes a stabilizing agent that includes PEG-20 glyceryl-oleoricinoleate. In another example, a composition according to the present disclosure includes a stabilizing agent that includes one or more sodium salts of di-propyl-, di-butyl-, di-pentyl-, di-hexyl-, di-heptyl-, di-octyl-, di-nonyl-, and/or di-decyl-sulfosuccinate. In yet another example, a composition according to the present disclosure includes a stabilizing agent that includes an isooctyl-sulfosuccinate.

It has been observed that inclusion of a moist keeping agent may enhance effectiveness of the stable pesticide composition. In one exemplary aspect, a moist keeping agent may enhance the moistening ability of a composition according to the present disclosure and allow a substrate treated with the composition to be moistened better. In another example, admixing the emulsifying and/or stabilizing substances can create a better homogeneity and a higher stability of the composites.

In one example, one or more stabilizing agents are present in an amount of about 0.1 wt. % to about 25 wt. %. In yet another example, one or more stabilizing agents are present in an amount of about 0.5 wt. % to about 5 wt. %. In still another example, one or more stabilizing agents are present in an about of about 21 wt. %.

In one embodiment, one or more stabilizing agents are selected in combination with the selection of a pesticide, a chitin skeleton destructive compound, and/or a vegetable oil to provide the pesticide composition with a high level of storage stability. A storage stable pesticide composition maintains a high level of effectiveness during storage. A storage stable pesticide composition also maintains component integrity during storage (e.g., components, such as vegetable oil, do not break down). In one example, such a pesticide composition has no measurable loss of effectiveness when stored at a temperature from about 5 degrees Celsius (° C.) to about 40° C. at a humidity level between about 45% and 85% for at least about 2 years. In another example, such a pesticide composition has no measurable loss of effectiveness when stored at a temperature of about 15° C. to about 30° C. at a humidity level of about 95% for at least about 2 years. Depending on the particular components chosen for a storage stable pesticide composition according to the present disclosure, the components may separate from one another during the storage stability period without impacting the effectiveness of the composition against pests upon application. In such a case, simple stirring of the composition should disperse the components in the composition.

A pesticide composition according to the present disclosure also has an appropriate stability after application that allows for effectiveness of the composition in eliminating the pest that is the target of the composition. In one example, a pesticide composition according to the present disclosure has an after-application-stability that allows the composition to be effective long enough to have an impact on the target pest. In another example, such a pesticide composition may break down at a time after effectiveness to the target pest such that it does not provide a long-term accumulated contamination in the environment (e.g., groundwater, food chain). In yet another example, a composition according to the present disclosure has an effectiveness of eliminating one or more target pests for at least about 25 days after application, thereafter the composition breaks down to have no negative impact on the environment. In still another example, a composition according to the present disclosure has an effectiveness of eliminating one or more target pests for at least about 10 days after application, thereafter the composition breaks down to have no negative impact on the environment.

In an alternative embodiment, a pesticide composition according to the present disclosure may include an ecologically-friendly disinfectant. Examples of an ecologically-friendly disinfectant include, but are not limited to, hydrogen peroxide, a quaternary ammonium composite, peroxy acid, a reaction product of a coconut fatty acid with a diethanolamine, bronopol, 1,3-Didecyl-2 methylimidazolium chloride, alkyl di-azapentane, alkylaminoglycine, an alkyl betaine, coco-betain-amidoamphopropionate, a parabene, sorbic acid, a salt of a sorbic acid, an ester of a sorbic acid, undecylenamide DEA, and any combinations thereof. In one example, a pesticide composition according to the present disclosure includes an ecologically-friendly disinfectant that includes one or more of a quaternary ammonium compound with a CAS-number 68391-01-5, 68424-85-1, 68424-95-3, 68989-01-5, 85409-22-9, 85409-23-0, and 100085-64-1. In another example, a pesticide composition according to the present disclosure includes an ecologically-friendly disinfectant that includes a peroxy acid, such as a peroxy acetic acid and/or a peroxy benzoic acid. In yet another example, a pesticide composition according to the present disclosure includes an ecologically-friendly disinfectant that includes a reaction product of a coconut fatty acid with a diethanolamine. In one example, a reaction product of a coconut fatty acid with a diethanolamine is a reaction product having the CAS-number 68440-04-0. In still another example, a pesticide composition according to the present disclosure includes an ecologically-friendly disinfectant that includes one or more of a methyl-, ethyl- and propyl parabene. In still yet another example, a pesticide composition according to the present disclosure includes an ecologically-friendly disinfectant that includes hydrogen peroxide, sodium benzoate, succinic acid, sorbic acid, ascorbic acid, and peracetic acid.

In one example, a disinfectant may be present in an amount of about 0.1 wt. % to about 50 wt. %. In another example, a disinfectant may be present in an amount of about 10 wt. % to about 40 wt. %. In yet another example, a disinfectant includes 5 wt. % $H_2O_2$ to 25 wt. % $H_2O_2$, 0.1 wt. % sorbic acid to 5 wt. % sorbic acid, 0.3 wt. % ascorbic acid to 10 wt. % ascorbic acid, and 0.2 wt. % peracetic acid to 7.5 wt. % peracetic acid.

In yet another embodiment, a pesticide composition according to the present disclosure may additionally include reservatrol, usnic acid, and/or one or more substances from the group of the humic acids. Reservatrol is a natural material from the class of phytoalexins, which, e.g., occurs in grapes. Usnic acid is a natural antibiotic agent, which is obtained from lichen varieties of the genus usnea. Surprisingly, it has been shown that the admixture of reservatrol and/or usnic acid further improves the disinfectant properties of a pesticide composition. Humic acids are high-molecular chemical compounds, which form besides other humic substances during the decomposition of biological materials. This process is called humification. Humic acids are therefore a group of compounds. It has been shown, that by adding the substance mixtures, which in the market are commonly known as humic acids, the disinfectant properties of a pesticide composition can be significantly improved.

Reservatrol may be present in a composition according to the present disclosure in any amount either with or without usnic acid and/or one or more humic acids. In one example, reservatrol may be present in a composition according to the present disclosure in an amount of about 0.1 wt. % to about 15 wt. %. In another example, reservatrol may be present in a composition according to the present disclosure in an amount of about 0.6 wt. % to about 1.1 wt. %. Usnic acid may be present in a composition according to the present disclosure in any amount either with or without reservatrol and/or one or more humic acids. In one example, usnic acid is present in a composition according to the present disclosure in an amount of about 0.5 wt. % to about 0.8 wt. %. In another example, usnic acid is present in a composition according to the present disclosure in an amount of about 1.5 wt. % to about 25 wt. %. One or more humic acids may be present in a composition according to the present disclosure in any amount wither with or without reservatrol and/or usnic acid. In one example, one or more humic acids is present in a composition according to the present disclosure in an amount of about 0.1 wt. % to about 6.3 wt. %. In another example, one or more humic acids is present in an amount of about 0.5 wt. % to about 6 wt. %. In yet another example, one or more humic acids is present in an amount of about 2.5 wt. % to about 25 wt. %.

In an alternative embodiment, a disinfectant composition may be produced with or without the pesticide discussed above. It has been shown that by combining one or several disinfectant substances with one or several of the mentioned stabilizing agents, each as discussed above, a composition can be created, which on one hand does without the use of persistent and ecologically and respectively toxicologically questionable disinfectants, but on the other hand displays a long-lasting disinfectant effect and offers a reliable defense against microorganisms. Surprisingly, it has been shown that a pesticidal composition with a disinfectant, or a disinfectant composition without a pesticide component, according to the present disclosure exhibits an unusually high stability in comparison to so far known, similarly put together disinfectants. Such a composition also exhibits excellent bactericidal effect, as well as very good fungicidal and virocidal properties.

One exemplary pesticide composition includes geraniol, PEG-20 glyceryl-oleoricinoleate, the reaction product of coconut fatty acids with diethanolamine, isooctylsufosuccinate, and soybean oil. Such an exemplary pesticide composition has shown exceptional stability and pesticidal and disinfectant effectiveness. Another exemplary pesticide composition showing exceptional stability and effectiveness includes:
 10-30 wt. % geraniol;
 5-25 wt. % PEG-20 glyceryl-oleoricinoleate;
 20-40 wt. % of the reaction product of coconut fatty acids with diethanolamine;
 10-30 wt. % isooctyl-sulfosuccinate; and
 1-20 wt. % soybean oil.

In another embodiment, a pesticide composition according to the present disclosure may also include one or more plant essences. In one exemplary aspect, it has been shown that the addition of one or more plant essences may significantly improve the pesticidal and/or disinfectant properties of a composition beyond that which would be expected. For example, the addition of these plant essences enhance the effectiveness of the composition, though the essences themselves have only shown to an insignificant extent to possess disinfectant and/or pesticidal properties. Without wanting to commit to a theory, the applicant postulates that the improvement of the disinfectant and/or insecticidal properties by including specific plant essences may be based, at least in part, on those plant essences stabilizing the composition, in synergistic interaction with other ingredients of the composition, to a significant extent, and thereby prolonging the period of effectiveness.

Examples of plant essences (i.e., botanicals) that improve the pesticidal and/or disinfectant properties of a composition of the present disclosure include, but are not limited to, *mentha piperita* (peppermint), *lavendula officinalis* (lavender), *rosa damascena* (rose), *calendula officinalis* (calendula), *hypericum perforatum* (Saint-John's-Wort), *achillea millefolium* (milfoil), *chamomilla matricaria* (chamomile), *urtica dioica* (nettle), *betula pendula* (common birch), and any combinations thereof. Plant essences may be used in a variety of forms. In one example, one or more plant essences are included in a composition of the present disclosure as one or more plant essences dissolved in alcohol. In another example, one or more plant essences are included in a composition of the present disclosure as one or more plant essences dissolved in a butylenes glycol-water mixture. In yet another example, a plant essence may be retrieved from a biological source via extraction from ground-up, crushed, or kibbled leaves, stalks, stems, and/or other parts of plants. An example source of supply for such plant essences is M&G Cosmetic Inc. of East Quoque, N.Y.

One or more plant essences may be included in a composition of the present disclosure in an amount based on the combination and amounts of other components of the composition to provide an enhanced effectiveness, while retaining stability, of the composition. In one example, one or more plant essences are present in a composition of the present disclosure in an amount of about 0.1 wt. % to about 10 wt. %. In yet another example, one or more plant essences are present in a composition of the present disclosure in an amount of 0.1 wt. % to 10 wt. %. In still another example, one or more plant essences are present in a composition of the present disclosure in an amount of about 1 wt. % to about 5 wt. %. In still yet another example, one or more plant essences are present in a composition of the present disclosure in an amount of 1 wt. % to 5 wt. %.

Another exemplary pesticide composition includes geraniol, PEG-20 glyceryl-oleoricinoleate, a reaction product of coconut fatty acids with di-ethanolamide, isooctyl-sulfosucchinate, soybean oil, plant essences of *mentha piperita* (peppermint), *lavendula officinalis* (lavender), *rosa damascena* (rose), *calendula officinalis* (calendula), *hypericum perforatum* (Saint-John's-Wort), *achillea millefolium* (milfoil), *chamomilla matricaria* (chamomile), *urtica dioica* (nettle) and/or *betula pendula* (common birch).

Yet another exemplary stable and effective pesticide composition includes:
 10-30 wt. % geraniol,
 5-25 wt. % PEG-20 glyceryl-oleoricinoleate,
 20-40 wt. % of the reaction product of coconut fatty acids with di-ethanolamine,
 10-30 wt. % isooctyl-sulfosuccinate,
 1-20 wt. % soybean oil, and
 one or more plant essences:
  0.1-1 wt. % of an essence of *mentha piperita*,
  0.1-1 wt. % of an essence of *lavendula officinalis*,
  0.1-1 wt. % of an essence of *rosa damascena*,
  0.1-1 wt. % of an essence of *calendula officinalis*, 0.1-1 wt. % of an essence of *hypericum perforatum*,
0.1-1 wt. % of an essence of *achillea millefolium*,
0.1-1 wt. % of an essence of *chamomilla matricaria*,
0.1-1 wt. % of an essence of *urtica dioica* and/or
0.1-1 wt. % of an essence of *betula pendula*.

A pesticide composition may additionally include one or more further gelatinizing substances. Example gelatinizing substances include, but are not limited to, paraffin wax, beeswax, honey, corn syrup, cellulose carboxy-methylether, guar gum, carob gum, tracanth gum, pectin, gelatine, agar, cellulose carboxy-methylether sodium salt, cellulose, cellulose acetate, dextrines, cellulose-2-hydroxyethylether, cellulose-2-hydroxypropylether, cellulose-2-hydroxypro-pylmethylester, cellulosemethylether, cornstarch, sodium alginate, maltodextrin, xanthan gum, epsilon-caprolactampolymer, diatomeen soil, acrylic acid polymers, PEG-30 glyceryl-cocoat, PEG-200, hydrogenated glyceryl-palmitate, and any combinations thereof. In one example, an acrylic acid polymer is an acrylic acid polymer that is sold under the brand name Carbomar by the company Degussa.

By using gelatinizing agents, a higher viscosity of the ready-made mixtures may be achieved. Such a higher viscosity has been shown in examples to enable a better and longer lasting adhesion of a pesticidal composition to the surface of the substrates to be treated.

Example pesticidal compositions formulated as described herein do not show any meaningful toxicity, teratogenicity or cancerogenicity. Exemplary compositions of the present disclosure have been shown to be non-acute toxic after inhalation by mammals, to have good local compatibility on mammalian skin, to be chronic oral non-toxic for a dosage period of at least 150 days, and acute meaningless fish toxic. Furthermore, exemplary pesticidal compositions may be utilized as a contact poison, which means that the composites do not penetrate e.g. fruits, but that the agents only take effect on the surface where insects are killed by coming into contact with the composition.

A pesticide composition according to the present disclosure may be utilized in a variety of concentrations. In one example, a pesticide composition according to the present disclosure may be provided as a concentrate having components at the concentrations described herein. In another example, a pesticide composition provided as a concentrate may be applied directly to a substrate (e.g., a plant, air) such that it may come into contact with a target pest. In yet another example, a pesticide composition provided as a concentrate may be diluted (e.g., emulsified) into water and/or one or more other agents. In such an example, composition component weight percentages as described herein may be adjusted accordingly. For example, a composition as a concentrate including the following components:

10-30 wt. % geraniol;
5-25 wt. % PEG-20 glyceryl-oleoricinoleate;
20-40 wt. % of the reaction product of coconut fatty acids with diethanolamine;
10-30 wt. % isooctyl-sulfosuccinate; and
1-20 wt. % soybean oil may be diluted, for example, to a $1/10^{th}$ dilution with water (e.g., 1 part pesticide concentrate to 9 parts water) to yield a composition including:

1-3 wt. % geraniol;
0.5-2.5 wt. % PEG-20 glyceryl-oleoricinoleate;
2-4 wt. % of the reaction product of coconut fatty acids with diethanolamine;
1-3 wt. % isooctyl-sulfosuccinate; and
0.1-2 wt. % soybean oil.

In one exemplary aspect, an exemplary pesticide composition with disinfectant properties (e.g., antifungal, antibacterial, etc.) may have an added advantage of mitigating microbial activity in impure water used for dilution. Such a benefit may be useful in applications where clean water supplies are not available (e.g., developing areas of the world).

In still another example, a pesticide composition according to the present disclosure may be provided having components at the concentrations described herein and utilized directly as provided. A pesticide composition according to the present disclosure may be applied to a substrate in any known method of application. Application techniques include, but are not limited to, direct application to a substrate, fumigation application technique, and any combination thereof.

In one example, a composition of the present disclosure is diluted at a ratio of about 1:5 to about 1:1500 prior to application (e.g., being deployed via fumigation). In another example, a composition of the present disclosure is diluted at a ratio of about 1:100 to about 1:750. In yet another example, a composition of the present disclosure is diluted at a ratio of about 1:250 to about 1:500.

A pesticide composition as discussed herein may be used directly on humans and/or other animals. Such a composition may also be used on surfaces and on objects. An additional advantage exists for exemplary compositions in the fact that they can also be dispensed via fumigation devices, which is especially an advantage in treating for a fungal pest. Up to now the application of fungicidal compositions was not possible via fumigation devices. In use in the agrarian sector (e.g., in which the fungicidal effectiveness often is in the center of attention) a further advantage lies in the fact that, based on the ecological harmlessness and the low toxicity, the usual waiting period does not have to be observed until the products are suitable for consumption. An additional advantage exists in the fact that based on the ecological harmlessness of the substances included in exemplary compositions, the application of the composition pursuant to the present disclosure can happen at any time, which makes it possible to apply at the time of the maximum biological effectiveness, e.g., the maximum growth spurt of harmful fungi. With conventional agents this is often not possible, because strict rules concerning the time of application do exist.

Exemplary compositions according to the present disclosure show a variety of advantages compared to pesticides known so far. In one example, a pesticide composition as described herein allows the treatment of several types of pests at the same time. So far, this was only possible in the prior art in a limited way, because e.g. insecticides and fungicides could typically not be mixed with each other. Therefore, further advantages achieved here are in terms of economy of time and improved profitability. Furthermore, pesticide compositions encompassed by the present disclosure do not lead to any noteworthy resistances.

Exemplary compositions as described herein further have the advantage that they can be used without concern inside households and without having to evacuate humans or animals. A further advantage exists in the fact that exemplary compositions show a significantly lowered allergy potential compared to conventional disinfectants. This is especially important in the immediate application to the skin, especially, if the application occurs with people who regularly come in contact with disinfectants, such as hospital staff and cleaning crews. Furthermore, it was shown that exemplary compositions according to the present disclosure did not lead to any noteworthy build-ups of resistances, which is a further advantage compared to the conventional disinfectants.

In another exemplary aspect, based on the strong disinfectant and/or pesticidal properties combined with the ecological and toxicological innocuousness of the compositions as described herein, as well as the high stability, the compositions are especially suited for the use in fighting pest insects in large areas. In contrast to conventional agents, a pesticide composition as described herein can be applied to large areas without causing danger for the humans living in that area or danger of ecological damages. Here, the fight against locusts can be seen as a typical field of application, particularly the fight against locusts on the ground shortly after hatching, therefore before the dreaded formation of swarms.

Furthermore, it has been shown that exemplary composition as described herein possess an outstanding suitability as a repellent. Such repellents serve to repel insects and/or other pests. A common field of application of repellents is that of a preventative measure to repel insects in areas with a high risk of malaria infection. But also in areas without the threat of malaria the usage of repellents, e.g. for repelling of ticks, is often a wise precautionary measure. Traditional pesticide compositions are often toxicologically inappropriate for application to mammalian skin for the purpose of repelling pests, such as mosquitoes. In one example, a pesticide composition according to the present disclosure provides very good repellent properties from insects for at least about 8 hours. In another example, a pesticide composition according to the present disclosure provides very good repellent properties from insects for at least about 6 hours.

Moreover, it has been shown that exemplary compositions according to the present disclosure can also be excellently used to treat head lice (pediculi). By applying the composite to the skin, hair and nails, excellent treatment results against virus, fungi, and bacteria can be achieved. This means that the compositions are also appropriate for the use as an active pharmaceutical substance. A method of treating head lice by applying such a composition, as well as the use of the composition for the manufacture of a pharmaceutical composite for the treatment of head lice are contemplated herein.

The non-toxic, ecologically-safe aspects coupled with the strong disinfectant and antifungal/antimold properties allow exemplary compositions of the present disclosure to be effective in a wide variety of additional applications. Example additional applications include, but are not limited to, as a medical industry disinfectant, as a water treatment (e.g., industrial water disinfection, drinking water disinfection, pool water treatment), as a household disinfectant, and any combinations thereof. In one example aspect, a composition of the present disclosure may be used in the treatment of water without negative impact on people (e.g., swimmers), animals, or the environment. It should be noted that typical pesticide compositions of the prior art would not be able to be used interchangeably as a strong disinfectant/anti-fungal/antimold agent due to the negative impacts toxicologically, environmentally, etc. on people, animals, and their environment. Exemplary composition of the present disclosure may include a pesticide and yet still be used as a non-toxic disinfectant (e.g., as water treatment). Exemplary compositions of the present disclosure do not have chlorine. Additionally, exemplary compositions have been shown to prevent deposit buildup in water treatment and water containment structures.

The invention is illustrated further by means of examples:

EXAMPLE 1

Production of a Disinfectant Composite

A disinfectant composition was produced by mixing the following ingredients:

| | |
|---|---|
| $H_2O_2$ | 5-25 wt. % |
| Sorbic acid | 0.1-5 wt. % |
| Ascorbic acid | 0.3-10 wt. % |
| Peracetic acid | 0.2-7.5 wt. % |
| Water | to 100 wt. % |

The described composite has proven to be an excellent disinfectant during tests.

EXAMPLE 2

Production of a Disinfectant Composite

A disinfectant composition was produced by mixing the following ingredients:

| | |
|---|---|
| $H_2O_2$ | 15.00 wt. % |
| Sorbic acid | 1.00 wt. % |
| Ascorbic acid | 3.00 wt. % |
| Peracetic acid | 2.75 wt. % |
| Water | to 100 wt. % |

The described composite has proven to be an excellent disinfectant during tests.

EXAMPLE 3

Production of an Insecticidal Composite

A pesticide composition was produced by mixing the following ingredients in the declared weight proportions:
- 10-30 wt. % geraniol;
- 5-25 wt. % PEG-20 glyceryl-oleoricinoleate;
- 20-40 wt. % of the reaction product of coconut fatty acids with diethanolamine;
- 10-30 wt. % isooctyl-sulfosucchinate; and
- 1-20 wt. % soybean oil.

The described composite has proven to be an excellent insecticide during tests.

EXAMPLE 4

Production of an Insecticidal Composite

A pesticide composition was produced by mixing the following ingredients in the declared weight proportions:
- 21 wt. % geraniol;
- 16 wt. % PEG-20 glyceryl-oleoricinoleate;
- 31 wt. % of the reaction product of coconut fatty acids with diethanolamine;
- 21 wt. % isooctyl-sulfosucchinate; and
- 11 wt. % soybean oil.

The described composite has proven to be an excellent insecticide during tests.

EXAMPLE 5

Production of an Insecticidal Composite

Various example pesticide compositions were produced by combining a composition according to example 1 and a composition according to example 3. Examples included combinations in a variety of ratios of combination. For example, ratios of combination may include 2 parts example 1 with 8 parts example 3 to 8 parts example 1 with 2 parts example 3. It should be noted that such a combination composition may also be further diluted (e.g., with water) to a variety of dilutions depending on the desired use. One example combination includes a 1:1 mixing ratio of the composition of example 1 with the composition of example 3:

- 5-15 wt. % geraniol;
- 2.5-12.5 wt. % PEG-20 glyceryl-oleoricinoleate;
- 10-20 wt. % of the reaction product of coconut fatty acids with diethanolamine;
- 5-15 wt. % isooctyl-sulfosuccinate; and
- 0.5-10 wt. % soybean oil
- 2.5-12.5 wt. % $H_2O_2$
- 0.05-2.5 wt. % Sorbic acid
- 0.15-5 wt. % Ascorbic acid
- 0.1-3.725 wt. % Peracetic acid
- Water to 100 wt. %.

The described composite has proven to be an excellent insecticide during tests.

EXAMPLE 6

Manufacturing of a Further Insecticidal Composition

A pesticide composition was produced by mixing the following ingredients in the named weight percentages:
- 10-30 wt. % geraniol;
- 5-25 wt. % PEG-20 glyceryl-oleoricinoleate;
- 20-40 wt. % of the reaction product of coconut fatty acids with diethanolamine;
- 10-30 wt. % isooctyl-sulfosuccinate;
- 1-20 wt. % soybean oil; and
- one or more plant essences:
    - 0.1-1 wt. % of an essence of *mentha piperita;*
    - 0.1-1 wt. % of an essence of *lavendula officinalis;*
    - 0.1-1 wt. % of an essence of *rosa damascene;*
    - 0.1-1 wt. % of an essence of *calendula officinalis;*
    - 0.1-1 wt. % of an essence of *hypericum perforatum;*
    - 0.1-1 wt. % of an essence of *achillea millefolium;*
    - 0.1-1 wt. % of an essence of *chamomilla matricaria;*
    - 0.1-1 wt. % of an essence of *urtica dioica*; and/or
    - 0.1-1 wt. % of an essence of *betula pendula.*

EXAMPLE 4

Execution of an Experiment in a Greenhouse Facility in Order to Ascertain the Pesticidal Properties The pesticidal properties of the composition according to example 6 were tested during an experiment in a greenhouse facility. The greenhouse facility in the experiment consisted of four greenhouses about 2,000 m² with a height of 4.5 m and one large greenhouse with a size of 12,000 m² and a height of 4 m.

The pesticide composition was deployed via fumigation in a dilution of 1:200. During the duration of the experiment fumigation took place 2 times per week. Through fumigation, already existing diseases caused by fungus or bacteria, as well as insect infestation, were completely eliminated. Furthermore, no further infestation occurred during the whole duration of the experiment. Especially surprising was the fact that during the treatment, mildew, which typically infests the leaves of the plants, was successfully combated. Such mildew infestation did occur before the use of the insecticidal compositions in a few unfavorable areas of the greenhouses, particularly in the wall rows and in unfavorable climate spots, e.g., the greenhouse exit. The infestation was fully cured by fumigation of the composition and no plant damage occurred.

EXAMPLE 6

Pesticidal Activity

The pesticidal properties of a composition according to example 3 were tested in the laboratory. The exemplary composition was tested at dilutions of 10% and 1% in a first trial with control; 0.1% 0.01%, 0.001% in a second trial with control, and 0.001% and 0.0001% with control in a third trial. The concentrations were by volume. The test included adding tap water to 1 L beakers so that after application of the exemplary composition the volume would be 1000 milliliters (ml) in each of three beakers for each concentration for each trial. Any chlorine present in the water was volatilized out of the water. Ten $2^{nd}$ and $4^{th}$ field-captured instar mosquito larvae being placed in each of the beakers. The exemplary composition was applied to three beakers for each concentration. For each trial three non-treated beakers served as experimental control. Observations were performed at 1, 2, 3, 4, 24, and 48 hours post-treatment. The number of dead larvae were recorded for each beaker at each time interval post-treatment. The mean number of dead larvae were calculated for each concentration at each time interval. The mean mortality for all concentrations of trial one was 100% after one hour. The mean mortality of larvae at 0.01% was 100% after 2 hours. In trial 2 at 0.001%, complete mortality occurred after 24 hours. In trial 3 at 0.001%, 90% mortality was observed at 48 hours. At 0.0001%, mean mortality was 73% after 48 hours. No mortality occurred in control beakers of trials 1 and 2. Trial 3 control beakers showed a mean mortality of 20% and 30% at 24 and 48 hours, respectively.

EXAMPLE 7

Pesticidal Activity

The pesticidal properties of a composition according to example 3 were tested in the field against various species of pests. In one set of tests, the exemplary composition was utilized at a concentration of 1.67% against adult pests and a concentration of 0.005% in swamps and puddles. The species treated included species of the subfamily Anophelinae, species of the subfamily Culicinae, species of the subfamily Toxorhynchitinae, amongst others. Lethality of adult pests was 100%. Growth inhibition of larvae was about 90%. Hatch inhibition of ovae was about 95%. In a second set of tests, the exemplary composition was utilized at a concentration of 1.67% sprayed with machine syringes directly on ground near swarming and landing locusts (*Locustana pardalina* and *Schistocera gregaria*) to determine mortality. A mortality rate of 100% was obtained within 3 hours.

EXAMPLE 8

Repellent Activity

The repellent properties of a composition according to the present disclosure were tested in the laboratory. The test included subjecting the arm of five human subjects to approximately 400 adult, female yellow fever mosquitoes of the genus *Aedes aegypti* in a breeding cage. The exemplary composition was tested against a reference composition of a commercial repellant product having 20% DEET as active ingredient. Each human subject was directly treated by having an area of approximately 250 cm² on their arms with the exemplary composition on one arm and the reference composition on another arm. The non-treated portions of the arms were covered with mosquito impervious tape. The hands of the subjects were covered with thick wool gloves, through which the mosquitoes could detect the human attractant receptor compounds emitted by all humans. The gloves protect the subjects from the mosquitoes attempting to bite. After administration of the compositions to the subjects, their arms were placed in the breeding cage for 10 minute intervals each hour. The number of mosquitoes landing on the glove and those approaching near the treated areas were estimated. The number of mosquitoes landing on the treated area and the number of mosquitoes biting the treated area were also measured. The exemplary composition provided complete protection from landing mosquitoes for up to 6 hours to 8 hours after application, depending on subject tested. During the same ten minute period about 100 to about 170 mosquitoes landed on the glove. The reference composition treatment provided complete protection from mosquito landing for up to about 2 hours to about 4 hours after application, depending on subject tested. The exemplary composition provided complete protection from biting by mosquitoes for up to about 7 hours to about 10 hours after application, depending on subject tested. The reference composition provided complete protection from biting by mosquitoes for up to about 2 hours to about 4 hours after application, depending on subject tested.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A stable non-toxic pesticide composition having fungicidal and insecticidal properties, the composition comprising:
   a pesticide that is nontoxic to mammals;
   one or more disinfectants;
   a vegetable oil; and
   one or more stabilizing agents;
   wherein said one or more stabilizing agents are selected and are present in an amount in combination with the selection and amount of said pesticide, said one or more disinfectants, and said vegetable oil to provide the composition with a stability upon application to a substrate effective to allow lethality against one or more target pests and wherein the composition is fungicidally and insecticidally effective upon application to a substrate and has a chitin skeleton destructive capability,
   wherein the composition comprises:
   5-15 wt. % geraniol;
   2.5-12.5 wt. % PEG-20 glyceryl-oleoricinoleate;
   10-20 wt. % of the reaction product of coconut fatty acids with a diethanolamine;
   5-15 wt. % isooctyl-sulfosuccinate;
   0.5-10 wt. % soybean oil;
   2.5-12.5 wt. % $H_2O_2$;
   0.05-2.5 wt. % Sorbic acid;
   0.15-5 wt. % Ascorbic acid; and
   0.1-3.725 wt. % Peracetic acid.

2. A composition according to claim 1, wherein said chitin skeleton destructive capability is due, at least in part, to a chitin skeleton destructive compound.

3. A composition according to claim 2, wherein said chitin skeleton destructive compound destabilizes one or more poly-n-acetylglucosamine structures of a chitin skeleton.

4. A composition according to claim 1, wherein the composition achieves about 100% effectiveness in lethality against one or more target pests at about 1 hour after application.

5. A composition according to claim 1, wherein said composition retains stability of lethal effectiveness against one or more target pests for at least 25 days.

6. A composition according to claim 1, wherein said composition retains stability of 100% lethal effectiveness against one or more target pests for at least 10 days.

7. A stable non-toxic pesticide composition having fungicidal and insecticidal properties, the composition comprising:
   a pesticide that is nontoxic to mammals;
   a chitin skeleton destructive compound;
   a vegetable oil; and
   one or more stabilizing agents;
   wherein said one or more stabilizing agents are selected and are present in an amount in combination with the selection and amount of said pesticide, said chitin skeleton destructive compound, and said vegetable oil to provide the composition with a stability upon application to a substrate effective to allow lethality against one or more target pests, and wherein the composition achieves about 100% effectiveness in lethality against one or more target pests at about 1 hour after application,
   wherein the composition includes:
   5-15 wt. % geraniol;
   2.5-12.5 wt. % PEG-20 glyceryl-oleoricinoleate;
   10-20 wt. % of the reaction product of coconut fatty acids with a diethanolamine;
   5-15 wt. % isooctyl-sulfosuccinate;
   0.5-10 wt. % soybean oil;
   2.5-12.5 wt. % $H_2O_2$;
   0.05-2.5 wt. % Sorbic acid;
   0.15-5 wt. % Ascorbic acid; and
   0.1-3.725 wt. % Peracetic acid.

8. A composition according to claim 7, further comprising one or more plant essences.

9. A stable non-toxic pesticide composition having fungicidal and insecticidal properties, the composition comprising:
   a pesticide that is nontoxic to mammals;
   one or more disinfectants;
   a vegetable oil; and
   one or more stabilizing agents;
   wherein said one or more stabilizing agents are selected and are present in an amount in combination with the selection and amount of said pesticide, said one or more disinfectants, and said vegetable oil to provide the composition with a stability upon application to a substrate effective to allow lethality against one or more target pests and wherein the composition is fungicidally and insecticidally effective upon application to a substrate and has a chitin skeleton destructive capability,
   wherein the composition consists of:
   21 wt. % geraniol;
   16 wt. % PEG-20 glyceryl-oleoricinoleate;
   31 wt. % of a reaction product of coconut fatty acids with a diethanolamine;
   21 wt. % isooctyl-sulfosuccinate; and
   11 wt. % soybean oil.

10. A composition according to claim 9, wherein the composition achieves about 100% effectiveness in lethality against one or more target pests at about 1 hour after application.

11. A composition according to claim 9, wherein said composition retains stability of lethal effectiveness against one or more target pests for at least 25 days.

12. A composition according to claim 9, wherein said composition retains stability of 100% lethal effectiveness against one or more target pests for at least 10 days.

13. A composition according to claim 7, wherein said composition retains stability of lethal effectiveness against one or more target pests for at least 25 days.

14. A composition according to claim 7, wherein said composition retains stability of 100% lethal effectiveness against one or more target pests for at least 10 days.

* * * * *